United States Patent [19]

Nemoto et al.

[11] 4,330,561

[45] May 18, 1982

[54] COLORED GELATIN COVERING

[75] Inventors: Kaoru Nemoto; Toshichika Ogasawara; Sadao Bessho, all of Tokyo, Japan

[73] Assignee: Chugai Seiyaku Kabushiki Kaisha, Tokyo, Japan

[21] Appl. No.: 130,183

[22] Filed: Mar. 13, 1980

[30] Foreign Application Priority Data

Mar. 23, 1979 [JP] Japan .................................. 54/33386

[51] Int. Cl.$^3$ ................................................ A23L 1/04
[52] U.S. Cl. .................................... 426/140; 426/250; 426/540; 426/576; 260/117; 127/34; 424/37
[58] Field of Search ............... 426/250, 540, 576, 140; 260/117; 127/34; 424/37

[56] References Cited

U.S. PATENT DOCUMENTS

| 425,982 | 4/1890 | Christopher et al. | 426/576 |
|---|---|---|---|
| 2,191,352 | 2/1940 | Oprean | 426/576 |
| 2,427,857 | 9/1947 | Hamill | 426/576 |

FOREIGN PATENT DOCUMENTS

| 52-73280 | 12/1977 | Japan . | |
|---|---|---|---|
| 789844 | 1/1958 | United Kingdom | 426/576 |
| 1255391 | 12/1971 | United Kingdom | 426/576 |

*Primary Examiner*—Jeanette M. Hunter
*Attorney, Agent, or Firm*—Browdy and Neimark

[57] ABSTRACT

A gelatin covering for a substrate such as a food or drug incorporating the use of caramel from which substances with a molecular weight up to 10,000 have been removed. The caramel does not cause the water solubility of the gelatin covering to be lowered with the passage of time.

1 Claim, No Drawings

COLORED GELATIN COVERING

This invention relates to a gelatin covering, and more particularly, it relates to a gelatin covering containing caramel as a colorant.

Caramel is often used as a colorant in foods or drugs, particularly, drugs for oral administration. However, commercial caramel exhibits disadvantages when it is used as a colorant for gelatin covering. The solubility of the covering containing commercial caramel is substantially lowered or impaired with the passage of time which is not true of gelatin free of caramel.

In general, a method of preventing the decrease of solubility of a gelatin covering free from caramel by addition of tartaric acid, sorbitol, polyethylene glycol, or the like has been known. However, such method does not give satisfactory results in case caramel is used as a colorant.

On the other hand, it has been known that in soft gelatin capsules containing a large amount of glycerine as a softening agent, the use of a large amount of the softening agent prevents the solubility of the gelatin capsules from deteriorating. However, a gelatin capsule containing a large amount of glycerine is too soft for practical use.

After study for developing a new method of preventing deterioration of the gelatin covering containing caramel as a colorant, the inventors found that the use of caramel from which substances having a molecular weight up to about 10,000 had been removed gave a desired gelatin film, that is, the water-solubility of the film is lowered little or not at all with the passage of time. Then, the inventors continued their study to complete this invention.

The term "covering" used herein includes not only coating directly applied on the surface of a substrate such as a food or drug, but also film, sheet or plate covering the substrate. Therefore, capsule or microcapsule skin for a drug or the like is included in the covering of this invention.

One purpose of this invention is to provide gelatin covering the water-solubility of which is not substantially lowered with the passage of time.

Other purposes of this invention will become clear from the description of the specification and the claims.

According to this invention, various methods, including ultrafiltration, dialysis and gel filtration techniques, can be used for removing substances having a molecular weight up to 10,000 from commercial caramel.

The ultrafiltration technique is usually carried out in a conventional manner. For example, commercial caramel is diluted with an appropriate medium, preferably distilled water, to about 20 times the volume of the caramel, and the diluted mixture is passed through ultrafiltration membrane capable of removing substance with a molecular weight up to about 10,000 under a gas pressure of about 3 $Kg/cm^3$. If it is desired that the lower molecular weight substances be removed more completely, the filtration can be repeated.

The ultrafiltration membrane which is useful in this invention includes any commercially available ultrafiltration membrane so long as it does not have an adverse effect on the caramel. Exemplary membranes include those sold under the trade names of PM-10 (polysulfone polymer manufactured by Amicon Corporation), G-10T (polyelectrolytic complex of quaternarily aminated polystyrene and sulfonated trislyrene manufactured by Bio-Engineering Japan), and KP-OO (cellulose acetate manufactured by Eastman Chemical).

Dialysis technique which is useful in this invention can be carried out in a conventional manner. For example, commercial caramel, after being diluted with distilled water to an appropriate level, is subjected to dialysis against running distilled water.

Any conventional gel filtration technique is suitable for this invention. For example, commercial caramel is chromatographed with a column charged with a material sold under the trade name of Sephadex from Pharmacia Fine Chemicals Inc., more particularly, Sephadex G-15, Sephadex G-25, Sephadex G-50 or the like and, by use of distilled water as solvent, a portion of the flow-out just after being colored is recovered as desirably treated caramel.

Each of the techniques described above for removing substances with a molecular weight up to about 10,000 may be repeated or two or more different techniques may be combined if desired. The thus treated caramel exhibits a remarkably reduced level of absorption in the ultraviolet light region (200–400 nm) in comparison with that of an untreated commercial caramel.

Further, it has been confirmed that the treated caramel is free from 4-methylimidazole or the like and has low toxicity. Therefore, the caramel treated according to this invention is suitable as a colorant for both foods and drugs.

When the thus obtained caramel is incorporated as a colorant in gelatin to form gelatin film or plate, it does not exhibit time-dependent deterioration of its water solubility as opposed to a conventional product, and when stored, will remain in a stable state for a prolonged time.

This invention is further illustrated by the following Example and Experiments which should not be construed to limit the scope of this invention.

EXAMPLE

Commercial caramel was diluted with distilled water to a volume 20 times that of the caramel to be used and the diluted caramel (400 ml) was subjected to ultrafiltration under a gas pressure of 3 $Kg/cm^3$ with use of ultrafiltration membrane PM-10 (an aromatic polymer). After the filtration, 300 ml of additional distilled water was added to the filtrate and the ultrafiltration was repeated to give 100 ml of the treated caramel.

EXPERIMENT

By the following formula, a gelatin mixture was prepared.

| Compornent | Amount |
| --- | --- |
| gelatin | 150 g |
| glycerine | 45 g |
| potassium sorbate | 0.6 g |
| water | 450 ml |

The caramel treated as in Example (3 g) or commercial caramel (3 g) was added to the resulting gelatin mixture (100 ml) and the mixture was heated on a water bath until the temperature of the mixture reached 70° C. Then the mixture (40 g) was poured in a rectangular laboratory dish with a length of 23 cm and a width of 8 cm, and dried by allowing it to stand for 3 days to form a gelatin plate. After drying, the plate was cut into square pieces exactly 1 $cm^2$ and they were allowed to stand for three days at 25° C. and a relative humidity of 50%.

For the control, a gelatin plate was similarly prepared except that no caramel was used.

Disintegration property of each gelatin plate was determined by the procedure defined in the Revised Japanese Pharmacopoeia 9th Edition, 33 Disintegration Test (Capsule) by using the solution which was prepared by mixing sodium chloride (2.0 g), diluted hydrochloric acid (24.0 ml) and distilled water to form 1,000 ml of solution having a pH of about 1.2.

The results are shown in the Table below.

TABLE

| Accelerated Conditions | Sample plate | | |
| --- | --- | --- | --- |
| | Plate containing no caramel (Control) | Plate containing the treated caramel | Plate containing commerical caramel |
| Just after preparation | 6 min. 20 sec. | 6 min. 30 sec. | 6 min. 20 sec. |
| one week at 40° C. | 6 min. 30 sec. | 8 min. | 20 min. |
| one week at 50° C. | 6 min. 40 sec. | 10 min. 30 sec. | 60 min.* |

*The original form remains.

What is claimed is:

1. A gelatin covering consisting essentially of gelatin and a sufficient amount of caramel to provide a desired degree of coloring, said caramel being substantially free from substances with a molecular weight up to about 10,000, whereby said caramel does not cause the water solubility of the covering to be substantially lowered with the passage of time.

* * * * *